United States Patent [19]

Atkins

[11] Patent Number: 4,522,512
[45] Date of Patent: Jun. 11, 1985

[54] THERMAL CONDUCTIVITY MEASUREMENT METHOD

[75] Inventor: Ronald T. Atkins, West Lebanon, N.H.

[73] Assignee: The United States of America as represented by the Secretary of the Army, Washington, D.C.

[21] Appl. No.: 375,066

[22] Filed: May 5, 1982

[51] Int. Cl.³ .................. G01F 1/68; G01N 25/18
[52] U.S. Cl. .................................. 374/44; 73/204; 219/505; 364/557; 374/29
[58] Field of Search .................. 374/44, 43, 164; 219/505; 338/22

[56] References Cited

U.S. PATENT DOCUMENTS

| | | | |
|---|---|---|---|
| 2,362,344 | 11/1944 | Bauer et al. | 73/75 X |
| 2,475,138 | 7/1949 | Hood, Jr. et al. | 374/44 |
| 3,045,473 | 7/1962 | Hager, Jr. | 374/44 |
| 3,075,377 | 1/1963 | Lang | 374/44 |
| 3,552,185 | 1/1971 | Goode, Jr. et al. | 374/44 |
| 3,572,093 | 3/1971 | Butler, Jr. et al. | 374/44 |
| 3,759,083 | 9/1973 | Erickson et al. | 374/107 |
| 3,938,383 | 2/1976 | Sayer | 7./154 X |
| 4,024,751 | 5/1977 | Potrzebowski | 374/43 |
| 4,059,982 | 11/1977 | Bowman | 374/44 |
| 4,155,244 | 5/1979 | Bhattacharyya | 374/44 |
| 4,232,543 | 11/1980 | Eguchi et al. | 374/44 |
| 4,255,962 | 3/1981 | Ashman | 374/44 X |

OTHER PUBLICATIONS

Publ., "Thermal Conductivity of Cellular Plastics by Means of a Probe", ASTM D2326-64T, 1964, pp. 473-477.

Primary Examiner—Daniel M. Yasich
Attorney, Agent, or Firm—Darrell E. Hollis

[57] ABSTRACT

A method and apparatus for determining the bulk thermal conductivity of a particular material includes the steps of embedding a thermistor in the material for which the bulk thermal conductivity is to be measured, applying a small current from a constant current source to the thermistor, mathematically determining the temperature of the material, applying a larger current to the thermistor until a steady state thermal condition is obtained, calculating the thermistor resistance, and finally calculating the thermal conductivity of the material according to the formula $$\frac{0.2389\, I^2 R}{4\pi r_1(T_1 - T_2)}$$

where I is the large current, R is the thermistor resistance when heated by the larger current, $r_1$ is the radius of the thermistor glass bead, $T_1$ is the surface temperature of the glass envelope of the thermistor and $T_2$ is the homogenous temperature of material whose bulk thermal conductivity is to be measured.

16 Claims, 5 Drawing Figures

CALIBRATE

THERMAL CONDUCTIVITY MEASUREMENT METHOD

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

The present invention relates generally to the measurement of bulk thermal conductivity in a material, and more particularly pertains to a method for measuring such bulk thermal conductivity wherein a thermistor operates as both the temperature measurement sensor and the heat source.

Currently available methods and apparatus for making bulk thermal conductivity measurements typically employ the use of a special probe designed and built for that specific purpose, with such probe requiring special electronics also specifically designed to be used with the probe. These probes and their supporting electronics are relatively expensive and perform no function other than the reading of thermal conductivity. Additionally, if thermal conductivity measurements are required under conditions where the probe cannot be recovered, as for instance when the same is deeply buried in soil or in concrete while it is being "set up", use of these probes can become economically prohibitive.

For example, U.S. Pat. No. 3,938,383 to Sayer is directed to the detecting of thermal characteristics of a subsurface formation in sites by inserting a predetermined volume of a cryogenic material into the formation. From the information received by conducting energy tests and other calculations, the thermal conductivity of the formation can be determined. The apparatus of the invention includes the use of a specially designed vessel adapted to receive a selected quantity of a cryogenic material, such as liquid nitrogen, liquid helium or liquid argon, such substances being suited for the purpose of the invention in that they have extremely low temperatures and are caused to boil off or vaporize when subjected to higher temperatures. Further, the apparatus utilizes an array of detection equipment which includes a plurality of sensors or receivers adapted to receive the specific form of test energy discharged by a transmitter and in addition to the special probe vessel and receivers, the apparatus also includes the use of a multichannel amplifier, a multichannel recorder, a pulse generator and an operating electrical circuit. As such, it can be seen that this typical prior art thermal conductivity measurement apparatus and method is of a complex and uneconomical construction which is difficult to set up and operate.

Another example of a prior art apparatus for determining bulk thermal conductivity is to be found in U.S. Pat. No. 4,155,244, to Bhattacharyya, wherein a test specimen may be placed between hot and cold plates, and a heat flow sensing means may then be placed intermediate the test material so as to form two portions of the test specimen. A guarded hot plate measurement of the heat flow to the hot plate enables calibration of the sensitivity of the specimens and the heat flow sensing means. The apparatus is then calibrated for measurement of other specimens of like physical properties. As is apparent, this apparatus can be effectively utilized only in those situations where a material of similar property to the material being tested is available so that a calibration of the apparatus can be achieved before the thermal conductivity measurement is taken.

Also of interest is U.S. Pat. No. 3,552,185, to Goode, Jr., et al, wherein a fixed thermal difference across a sample is accomplished by placing the sample between two surfaces whose temperatures are accurately controlled. The cold plate temperature is set and controlled by a thermoelectric heat pump driven by a high-gain proportional controller, while the hot plate is concurrently operated at a controlled temperature with the heat thereto being supplied from a close-coupled proportionally controlled low mass heater. The heat flow through the sample is measured with a heat flow transducer which produces an EMF that is proportional to the heat flow per unit time and area through the material, with the EMF thus derived being the voltage divided by a slide wire which is mechanically coupled to an in-place thickness indicator. Appropriate analog corrections are made to provide a signal for direct digital read-out of the thermal conductivity associated therewith. Inasmuch as the device utilizes a silicon controlled rectifier system, separate heaters, thermoelectric transducers, digital voltmeters and hot and cold thermometer probes, it can be seen that the same is of a complex construction which is uneconomical to manufacture and which is difficult to set up and utilize.

As can be appreciated then, there is a continuing need for new and improved apparatuses and methods for measuring bulk thermal conductivity which employ the use of simple and economical measuring equipment and associated techniques.

SUMMARY OF THE INVENTION

In accordance with the present invention, there is provided a method and associated apparatus for measuring bulk thermal conductivity which has all the advantages of the prior art bulk thermal conductivity measurement apparatuses and methods and which has none of the disadvantages. To attain this, the present invention provides for the use of a thermistor, a current source and a voltage readout device wherein the thermistor operates as both a temperature measurement sensor and the heat source. Specifically, the invention utilizes a commercially available thermistor as the probe with the equipment being utilized to take the measurement being a variable constantcurrent source and a digital multimeter or other voltage readout device such as a strip chart recorder.

With the thermistor embedded in the material whose thermal conductivity is to be measured, a small current is applied to the thermistor and the voltage across the thermistor may then be read. From this, the resistance of the thermistor may be calculated and the homogenous temperature of the material determined. A larger current is then applied to the thermistor and the voltmeter is monitored until its reading is stable, thus indicating a steady state thermal condition. The resistance value for the thermistor may then be calculated and the new temperature determined. This resistance value may then be used to calculate the thermal energy being added to the material and a mathematical procedure is employed, along with the calibrating of the thermistor with two known materials to determine the thermal conductivity of the test material. In an alternative embodiment of the invention, a variable voltage source and a second digital multimeter may be substituted for the constant current source.

It is therefore an object of the present invention to provide a method for measuring bulk thermal conductivity of a material.

It is another object of the present invention to provide an economical, speedy and simplified method for determining the bulk thermal conductivity of a material.

Still another object of the present invention is to provide a method for measuring bulk thermal conductivity wherein the apparatus employed is accurate, reliable, and expendable in an in-situ environment.

Yet another object of the present invention is to provide a system for measuring bulk thermal conductivity which is durable, efficient, portable and lightweight construction.

Even another object of the present invention is to provide for a bulk thermal conductivity measurement device where a thermistor operates both as the temperature measurement sensor as well as the heat source.

Other objects, advantages and novel features of the present invention will become apparent from the following detailed description of the invention when considered in conjunction with the accompanying drawings, in which:

DESCRIPTION OF THE PREFERRED EMBODIMENTS

Figure 1:
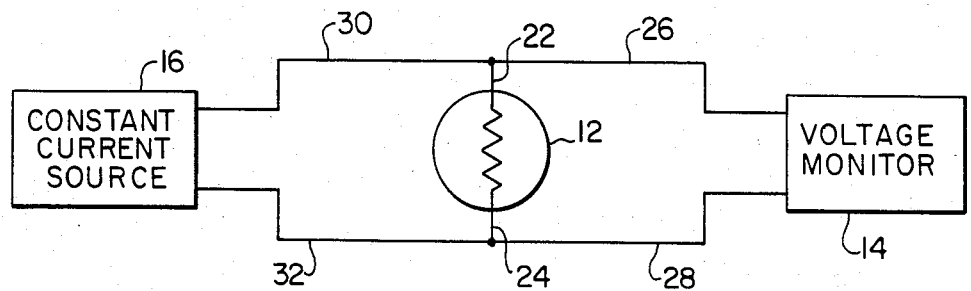
FIG. 1 is a schematic representation of a first embodiment of the present invention.
Figure 2:
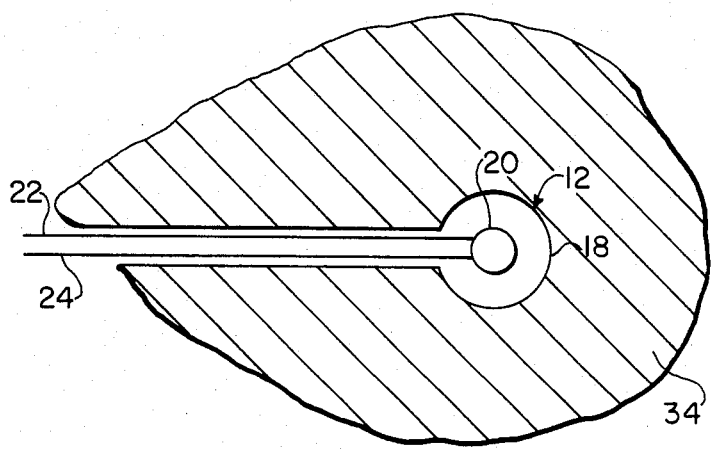
FIG. 2 is a plan view, partly in cross-section, of the thermistor associated with the present invention embedded in a material whose thermal conductivity is to be determined.

With reference now to the drawings and in particular to FIG. 1 thereof, there is illustrated a bulk thermal conductivity measurement device which includes a commercially available thermistor 12 in parallel electrical communication with a voltage monitoring means 14, such as a digital multimeter, and a constant current source means 16. As more clearly illustrated in FIG. 2, the thermistor 12 includes a glass envelope portion 18 surrounding an associated semiconductor bead 20. The bead 20 is provided with electrical connection means, such as wires 22, 24 extending outwardly therefrom. Referring concurrently to FIGS. 1 and 2, it can be seen that the electrical wires 22, 24 are respectively connectable to wires 26, 28 of the voltage monitoring means 14 and to wires 30, 32 associated with the constant current source means 16, thereby to establish the aforementioned parallel electrical communication.

In utilizing the present invention, thermistor 12 will be initially embedded in a surrounding material 34, as illustrated in FIG. 2, whose thermal conductivity is to be measured at some particular temperature. In effect, the thermistor 12 is utilized as a probe insertable into the material 34, while the constant current source means 16 should be a variable constant current source and the voltage monitoring means 14, which in this case has been described as being a digital multimeter, could be a strip chart recorder if desired. These instruments are general purpose in nature and are normally available in any well-equipped electronics laboratory.

The method used to make the thermal conductivity measurement of the material 34 is derived from the standard heat flow equations for spheres. In this respect, when the thermistor's semiconductor bead 20 is heated slightly, the steady state heat flow equation into the glass envelope 18 is:

$$Q = K_T \sqrt{A_o A_1} \left( \frac{T_0 - T_1}{r_1 - r_o} \right) \quad (1)$$

where
$Q$ = the thermal energy being added to the system, i.e., being generated in the semiconductor bead 20, in calories per second
$K_T$ = the thermal conductivity of the glass envelope 18 associated with the thermistor 12
$A_0$ = the surface area of the semiconductor bead 20
$A_1$ = the surface area of the glass envelope 18
$T_1$ = the surface temperature of glass envelope 18
$T_0$ = the surface temperature of the semiconductor bead 20
$r_0$ = the radius of the semiconductor bead (sphere) 20
$r_1$ = the radius of the glass envelope (sphere) 18

Since the surface area of a sphere is $4\pi r^2$ equation (1) can be reduced to $$Q = K_T 4\pi (T_0 - T_1) \frac{r_1 r_0}{r_1 - r_0} \quad (2)$$

If a sphere of test material 34 is assumed to surround the glass envelope 18 of the thermistor 12, then at steady state, the thermal energy flowing into the glass envelope 18 can be assumed to flow on into the test material 34 so that:

$$Q = K_M 4\pi (T_1 - T_2) \frac{r_2 r_1}{r_2 - r_1} \quad (3)$$

where
$K_M$ = the thermal conductivity of the material 34
$T_2$ = the temperature of the surface of the assumed sphere of material 34 being measured
$r_2$ = the radius of the sphere of the material 34

As can be appreciated, a solving of equation (3) for the thermal conductivity of the material, $K_M$, then results in:

$$K_M = Q \left( \frac{1}{4\pi(T_1 - T_2)} \right) \left( \frac{1}{r_1} - \frac{1}{r_2} \right) \quad (4)$$

If the volume of material 34 is so large that the radius $r_2$ can be assumed to be infinite with respect to $r_0$ and $r_1$, the above equation reduces to:

$$K_M = \frac{Q}{4\pi r_1 (T_1 - T_2)} \quad (5)$$

This equation can then be used to find the thermal conductivity of the material 34, provided that a value for $T_1$, the surface temperature of the glass envelope 18, can be found. Such a means is provided by equation (2), which, when solved for $T_1$ gives:

$$T_1 = T_0 - \frac{Q(r_1 - r_0)}{K_T 4\pi\, r_0\, r_1} \quad (6)$$

It should be noted that when the thermistor 12 is heated, the value of Q for both equations (5) and (6) can be found by the conventional equation:

$$Q = 0.2389 I^2 R_{HOT} \quad (7)$$

where

I = the constant current applied to the thermistor 12
$R_{HOT}$ = the resistance of the thermistor 12 when it is heated
Q = thermal energy being added to the system, in calories/second.

In summation, the thermistor 12 can be used to measure the thermal conductivity $K_M$ of a bulk material 34 by utilizing the following three equations:

$$Q = 0.2389 I^2 R_{HOT} (\text{or } 0.2389 IV) \quad (8)$$

$$T_1 = T_0 - \frac{Q(r_1 - r_0)}{K_T 4\pi\, r_0 r_1} \quad (9)$$

$$K_M = \frac{Q}{4\pi\, r_1 (T_1 - T_2)} \quad (10)$$

Accordingly, the method of the present invention permits a thermal conductivity measurement to be taken by first embedding the thermistor 12 in the material 34 and then applying a small current, on the order of 50 microamperes, to the thermistor, with the voltage across the thermistor then being read. From this, the resistance of the thermistor 12 is calculated (V/I) and the steady state homogenous temperature $T_2$ of material 34 determined, the thermistor resistance related to temperature.

A large current, on the order of 5 milliamperes, is then applied to the thermistor 12 and the voltmeter 14 monitored until its reading is stable which indicates a steady state thermal condition has been achieved. The resistance value $R_{HOT}$ for the thermistor 12 may then be calculated, the voltage divided by the current I, and the new temperature $T_0$ determined, the thermistor being the heat source in this instance adding thermal energy to the material.

Figure 4:
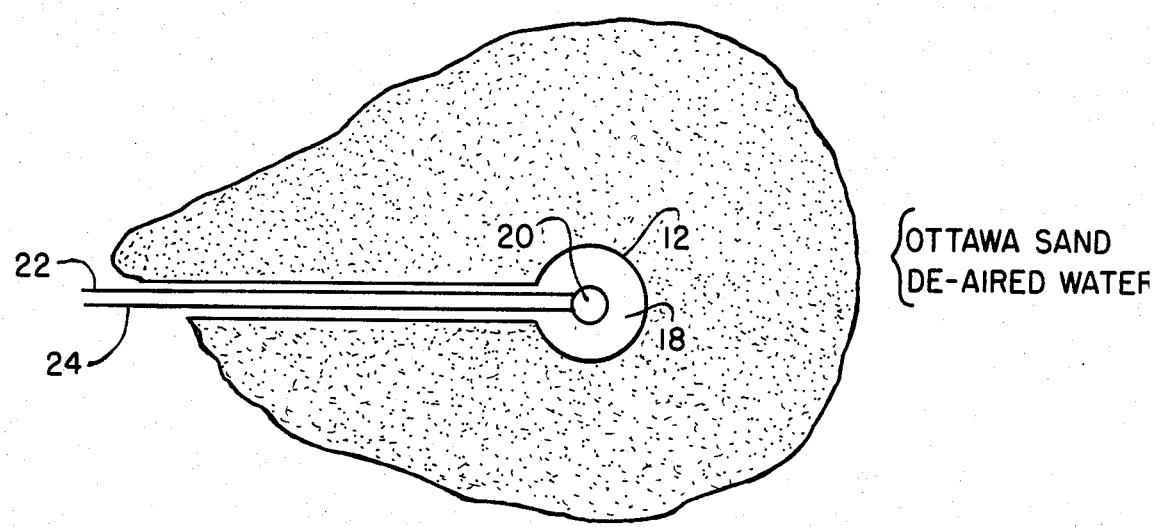
FIGS. 4 and 4a are views of the thermistor embedded in different materials.
Figure 4A:
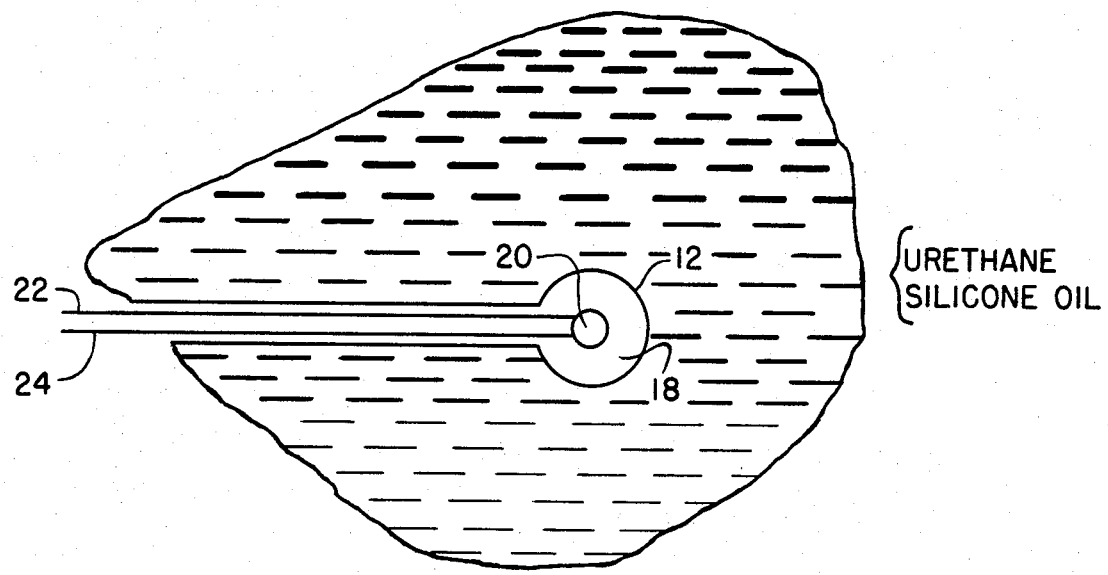

As is apparent, the above-described method establishes all unknowns in the equations except $r_1$ and $K_T$. The value of $r_0$ is readily determinable from the specification sheet of the specific thermistor employed. The values of $r_1$ and $K_T$ may be obtained by calibrating thermistor 12 with two known materials for which the thermal conductivity, $K_M$, is known and solving equation (5) with equation (6) substituted therein (two equations and two unknowns, $K_T$ and $r_1$). In FIGS. 4 and 4a, respectively, two materials which make reasonable calibration materials are de-aired water and silicone oil and two other materials which may be used for calibration are Ottawa sand and urethane. Since these are dry materials, possible errors due to convective heat flow are eliminated. Once $K_T$ and $r_1$ have been determined, the above equations are used to calculate $K_M$, the thermal conductivity of the material.

Figure 3:
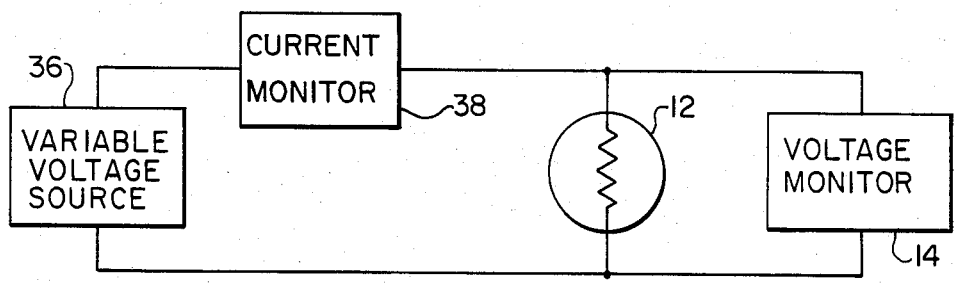
FIG. 3 is a schematic representation of a second embodiment of the present invention.

Referring next to FIG. 3 of the drawings, an alternative apparatus for performing the method of the present invention will be described. Briefly, a variable voltage source 36 and a current monitoring means 38, such as a digital multimeter, have been substituted for the constant current source 16 illustrated in FIG. 1. The multimeter 38 may be used to monitor the current to the thermistor 12 and the variable voltage source 36 can be used to adjust that current for the hot and cold readings. It is not necessary that the current be precisely set, only that it be precisely known and that it have self-heating in one case and not in the other. Additionally, as aforediscussed it is not necessary that a digital multimeter be used to read the voltage. A strip chart recorder has been used when unattended operation is desirable. Further, this method also is preferable when the test material 34 is changing temperature. Under these conditions, a timer/relay may be used to switch back and forth between two constant current sources at ten minute intervals, thus generating a continuous set of readings.

As can be appreciated, the method for measuring thermal conductivity as described above provides the advantage of requiring no special equipment dedicated specifically to such a purpose. All the equipment used with respect to the above invention is general purpose in nature and commercially available without resorting to manufacturers who specialize in thermal conductivity equipment. A further advantage is that the above-described apparatuses use a relatively inexpensive probe which therefore makes it much more attractive in applications where the probe is not recoverable such as in snow, ice and frozen ground. Such an arrangement, i.e., the use of a throw-away probe, is useful in research labs, highway and dam design, building material testing and monitoring, e.g., building insulation, moisture absorption. Further, the simplicity of the present invention is achieved through the use of a single device, the thermistor 12, as both the temperature measurement sensor and the heat source.

With respect to the above description then, it should be realized that the optimum dimensional relationships for the parts of the invention to include variations in size, shape, form, function and manner of operation, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as described by the claims appended hereto.

What is claimed as new and desired to be secured by Letters Patent of the United States is as follows:

1. A method for measuring bulk thermal conductivity ($K_m$) of a material comprising the steps of:
   a. embedding a small combined sensor and heat source having a heat bead surrounded by an envelope in a substantially large material;
   b. determining the temperature value of said material using said combined sensor and heat source;
   c. determining the thermal energy value (Q in calories per second) generated by said heat bead;
   d. determining the surface temperature value of said heat source envelope;

e. determining the radius value of said heat source envelope; and
f. calculating said thermal conductivity ($K_m$) by utilizing said determined values in the equation $$K_m = \frac{Q}{4\pi(T_1 - T_2)r_1}$$

where:
$Q$ equals the thermal energy in calories per second generated by said heat source and sensor
$T_1$ equals the surface temperature of said heat source envelope
$T_2$ equals the temperature of said material
$r_1$ equals the radius of said heat source envelope.

2. The method of claim 1 further including the step of applying a second current to said heat source, said applying step executed after said material temperature determining step and before said thermal energy determining step.

3. The method of claim 2 wherein the step of determining said generated thermal energy value (Q in calories per second) includes:
   a. determining the second voltage across said heat source;
   b. calculating the second resistance of said heat source by dividing said second current by said second voltage; and
   c. calculating the thermal energy generated by said heat bead by utilizing said determined values in the equation $$Q = 0.2389 I^2 R_{HOT}$$

where:
$I$ equals said second current
$R_{HOT}$ equals said second resistance.

4. The method of claim 2 wherein the steps heat source envelope temperature determining and heat source envelope radius determining include:
   a. determining the temperature of said heat bead;
   b. determining the radius of said heat bead
   c. providing two materials each having a known thermal conductivity
   d. calculating the thermal conductivity ($K_k$) of the envelope and the radius of the glass bead by using said two materials to determine the values $r_0$ and $T_0$ in the equations:

$$T_1 = T_o - \frac{Q(r_1 - r_0)}{K_T 4\pi r_0 r_1}$$

$$K_k = \frac{Q}{4\pi r_1(T_1 - T_k)}$$

where:
$Q$ equals the thermal energy generated by the heat bead
$T_1$ equals the surface temperature of the envelope
$T_0$ equals the surface temperature of the heat bead.
$r_1$ equals the radius of the envelope
$r_0$ equals the radius of the heat bead
$K_T$ equals the thermal conductivity of the envelope
$K_k$ equals the thermal conductivity of the two materials
$T_k$ equals the temperature of the two materials.

5. The method of claim 4 wherein the steps heat source envelope temperature determining and heat source envelope radius determining include the step of:
   a. calibrating said heat source with said two materials whose thermal conductivity is known;
   b. determining the thermal conductivity of the envelope $K_T$; and
   c. determining the radius $r_0$ of the heat bead.

6. The method for determining bulk thermal conductivity of a material as recited in claim 4 wherein said two known materials comprises Ottawa sand and urethane.

7. The method for determining bulk thermal conductivity of a material as recited in claim 4 wherein said two known materials comprises deaired water and silicone oil.

8. The method of claim 2 wherein the step of determining said generated thermal energy includes:
   a. determining the second voltage across said heat source;
   b. calculating the second resistance of said heat source by dividing said second current by said second voltage; and
   c. calculating the thermal energy generated by said heat bead by utilizing said determined values in the equation $$Q = 0.2389 I^2 R_{HOT}$$

where:
$I$ equals said second current
$R_{HOT}$ equals said second resistance.

9. The method of claim 2 wherein the steps heat source envelope temperature determining the heat source envelope radius determining include:
   a. determining the temperature of said heat bead;
   b. determining the radius of said heat bead
   c. providing two materials each having a known thermal conductivity
   d. calculating the thermal conductivity of the envelope and the radius of the glass bead by using the equation:

$$T_1 = T_o - \frac{Q(r_1 - r_0)}{K_T 4\pi r_0 r_1}$$

$$K_k = \frac{Q}{4\pi r_1(T_1 - T_k)}$$

where:
$Q$ equals the thermal energy generated by the heat bead
$T_1$ equals the surface temperature of the envelope
$T_0$ equals the surface temperature of the heat bead
$r_1$ equals the radius of the envelope
$r_0$ equals the radius of the heat bead
$K_T$ equals the thermal conductivity of the envelope
$K_k$ equals the thermal conductivity of the two materials
$T_k$ equals the temperature of the two materials.

10. The method of claim 2 wherein the steps heat source envelope temperature determining and heat source envelope radius determining include the step of:
    a. calibrating said heat source with two known materials whose thermal conductivity is known;
    b. determining the thermal conductivity of the envelope; and
    c. determining the radius of the heat bead.

11. The method of claim 1 further including the step of applying a first current to said heat source, said applying step executed after said embedding step and before said material temperature determining step.

12. The method of claim 11 wherein the step of determining the temperature of said material includes:
   a. determining the first voltage across said heat source; and
   b. calculating the first resistance of said heat source by dividing said first current by said first voltage.

13. The method of claim 11 wherein the step of determining the temperature of said material includes:
   a. determining the first voltage across said heat source; and
   b. calculating the first resistance of said heat source by dividing said first current by said first voltage.

14. The method for determining the bulk thermal conductivity of a material as recited in claim 1 wherein said heat source comprises a thermistor.

15. The method of claim 1 further including the steps of:
   a. applying a first current to said heat source, said applying step executed after said embedding step and before said material temperature determining step; and
   b. applying a second current to said heat source, said second current applying step executed after said material temperature determining step and before said thermal energy determining step.

16. The method of claim 15 wherein said second current is larger than said first current.

* * * * *